US012788989B2

(12) United States Patent
Bartlett et al.

(10) Patent No.: US 12,788,989 B2
(45) Date of Patent: Nov. 10, 2026

(54) REINFORCEMENT LEARNING BASED CLOSED-LOOP NEUROMODULATION SYSTEM

(71) Applicant: Purdue Research Foundation, West Lafayette, IN (US)

(72) Inventors: Edward Lee Bartlett, West Lafayette, IN (US); Brandon Steven Coventry, Verona, WI (US)

(73) Assignee: Purdue Research Foundation, West Lafayette, IN (US)

( * ) Notice: Subject to any disclaimer, the term of this patent is extended or adjusted under 35 U.S.C. 154(b) by 444 days.

(21) Appl. No.: 18/083,490

(22) Filed: Dec. 17, 2022

(65) Prior Publication Data

US 2023/0191130 A1 Jun. 22, 2023

Related U.S. Application Data

(60) Provisional application No. 63/290,993, filed on Dec. 17, 2021.

(51) Int. Cl.
*A61N 1/36* (2006.01)

(52) U.S. Cl.
CPC ..... *A61N 1/36139* (2013.01); *A61N 1/36146* (2013.01)

(58) Field of Classification Search
CPC ............ A61N 1/36139; A61N 1/36146; A61N 1/36135
See application file for complete search history.

(56) References Cited

U.S. PATENT DOCUMENTS

| | | | | |
|---|---|---|---|---|
| 7,231,254 B2 * | 6/2007 | DiLorenzo | A61N 1/3605 | 607/45 |
| 8,774,923 B2 * | 7/2014 | Rom | A61B 5/6846 | 607/45 |
| 2013/0066137 A1 * | 3/2013 | Hulvershorn | A61N 1/36071 | 600/13 |
| 2021/0308462 A1 * | 10/2021 | Carmena | A61N 1/3787 | |
| 2022/0143412 A1 * | 5/2022 | Paydarfar | A61N 1/36125 | |

(Continued)

OTHER PUBLICATIONS

Lee D, Seo H, Jung MW. Neural basis of reinforcement learning and decision making. Annu Rev Neurosci. 2012;35:287-308. doi: 10.1146/annurev-neuro-062111-150512. Epub Mar. 29, 2012. PMID: 22462543; PMCID: PMC3490621. (Year: 2012).*

(Continued)

*Primary Examiner* — Niketa Patel
*Assistant Examiner* — Attiya Sayyada Hussaini
(74) *Attorney, Agent, or Firm* — Purdue Research Foundation

(57) ABSTRACT

The neuromodulation system includes a sensor, a recording amplifier, a processor, and a stimulator. The neuromodulation system is configured to provide stimulation and control of an intended target. The processor utilizes a closed-loop feedback system which is configured to actively sense target brain states and apply corrective stimulation or feedback as dictated by its effectors. The processor implements reinforcement learning which creates real-time statistical models of current and recent past neural states which actively and automatically learns stimulation paradigms which create paths from pathological to nominal brain states.

19 Claims, 15 Drawing Sheets

(56) References Cited

U.S. PATENT DOCUMENTS

| | | | | |
|---|---|---|---|---|
| 2022/0152396 A1* | 5/2022 | Milosevic | ............ | A61N 1/0534 |
| 2023/0137595 A1* | 5/2023 | Rao | ........................ | G16H 50/20 |
| | | | | 607/59 |

OTHER PUBLICATIONS

Pineau J, Guez A, Vincent R, Panuccio G, Avoli M. Treating epilepsy via adaptive neurostimulation: a reinforcement learning approach. Int J Neural Syst. Aug. 2009;19(4):227-40. doi: 10.1142/S0129065709001987. PMID: 19731397; PMCID: PMC4884089. (Year: 2009).*

Chugh, Akshita. "MAE, MSE, RMSE, coefficient of determination, adjusted R squaredâwhich metric is better?. " Medium (2020). (Year: 2020).*

* cited by examiner

Sample Trial Evolutions in Spiker-Net

REINFORCEMENT LEARNING BASED CLOSED-LOOP NEUROMODULATION SYSTEM

CROSS REFERENCE TO RELATED APPLICATIONS

The present application is a U.S. non-provisional application which claims the benefit of U.S. provisional application Ser. No. 63/290,993, filed Dec. 17, 2021, the content of which is incorporated by reference herein in its entirety.

GOVERNMENT SUPPORT CLAUSE

This invention was made with government support under DC011580 awarded by the National Institutes of Health. The government has certain rights in the invention.

FIELD

The disclosure generally relates to medical devices and, more particularly, to neuromodulation and clinical and experimental neurosciences.

INTRODUCTION

This section provides background information related to the present disclosure which is not necessarily prior art.

Electrical stimulation of neural tissue dates to the 18th century in Luigi Galvani's experiments in frog nerves. Electrical stimulation as a therapeutic tool, now the major segment of the field of neuromodulation, gained prominence with the advent of the cochlear implant for restoration of hearing. Further advances found that implantation of stimulation electrodes into patient subthalamic nuclei provided efficacious treatment of Parkinsonian dyskinesia. This technique, known as deep brain stimulation, has since been extended to treat a wide variety of neurological and neuropsychiatric diseases and disorders, such as obsessive-compulsive disorder and epilepsy with other clinical trials in progress.

Clinical neuromodulation has not been a panacea, with patients often reporting abhorrent side-effects resulting in discontinuation of treatment. One problem with current clinical devices is their operation in open-loop conditions, in which the stimuli are set without regard to the changing conditions of their target, with constant high frequency stimulation. Such operating conditions could drive adaptation to the stimuli, recruitment of irrelevant and off-target neural circuits, and require repeated trips to the clinic for stimulation parameter adjustments.

Closed-loop systems, which actively sense patient biosignals and provide measured therapeutic stimuli, represent the most clinically successful devices such as the cardiac pacemaker and the insulin pump. Some effort has been made to implement closed-loop control in neuromodulation devices. However, these techniques have been limited to simple threshold measurements with binary stimulation (on/off only), largely agnostic to underlying neural dynamics and ignoring important features which could lead to better treatment of disease.

Accordingly, there is a need for a neuromodulation system that operates in a closed loop system which may actively sense and apply stimuli in response to patient brain states. Desirably, the neuromodulation system may also titrate and personalize stimulation to specific patient conditions and individual patients.

SUMMARY

In concordance with the instant disclosure, a neuromodulation system that operates in a closed loop system which may actively sense and apply stimuli in response to patient brain states and may also titrate stimulation to specific patient conditions, has been surprisingly discovered.

The neuromodulation system includes a sensor, a recording amplifier, a processor, and a stimulator. The neuromodulation system may be configured to provide stimulation and control of an intended target. The recording amplifier may be electrically coupled to the to the sensor. The recording amplifier may be configured to read and process stimuli, such as neural actively, detected by the sensor. The recording amplifier may be further configured to output a signal based on the processed stimuli. The processor may be communicatively coupled to the recording amplifier. The processor may execute steps to monitor the signal provided by the recording amplifier and output an instruction based on the signal. The stimulator may be communicatively coupled to the processor. The stimulator may be configured to provide a non-binary stimuli to the intended target based on the instruction from the processor. As a non-limiting example, the neuromodulation system may be configured to provide stimulation and control of a nervous system of a human or animal subject for the purpose of clinical restoration of neural function or basic science studies in neural dynamics. It should be appreciated that the present technology may be utilized in various fields such as studies for esophageal motility, epilepsy response, glucose moderation, vagus nerve stimulation, hormonal control, kidney uptake modulation, insulin control, deep brain stimulation, and brain-computer interfacing.

In certain circumstances, the neuromodulation system may include a kit. The kit may include a sensor, a recording amplifier, a processor, and a stimulator. In a specific example, one or more of the sensor, the recording amplifier, the processor, and the stimulator may be configured to be electrically coupled to another of the sensor, the recording amplifier, the processor, and the stimulator. In another specific example, one or more of the sensor, the recording amplifier, the processor, and the stimulator may be configured to wirelessly communicate to another of the sensor, the recording amplifier, the processor, and the stimulator.

Various ways of using the neuromodulation system are provided. Certain methods may include a step of providing the neuromodulation system according to a first method. The first method may include a step of observing and measuring the current state of the nervous system by use of the sensor. The sensor may be one of an implanted epicutaneous, optical, or similar sensor. Next, the processor may build and refine computational models of neural dynamics using a method of reinforcement learning. Then, corrective stimulations may be applied to the nervous system to steer activity towards a desired state. The corrective stimulations may include targeted electrical, optical, or similar stimulations. It should be appreciated that the system may reach a steady state after one or more iterations of corrective stimulations. Afterwards, a map may be created by the processor of stimulation to response relationships to maintain desired neural dynamics. In certain circumstances, the neuromodulation system may continue to augment and improve stimulation to neural response mappings according to the specific subject's needs.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
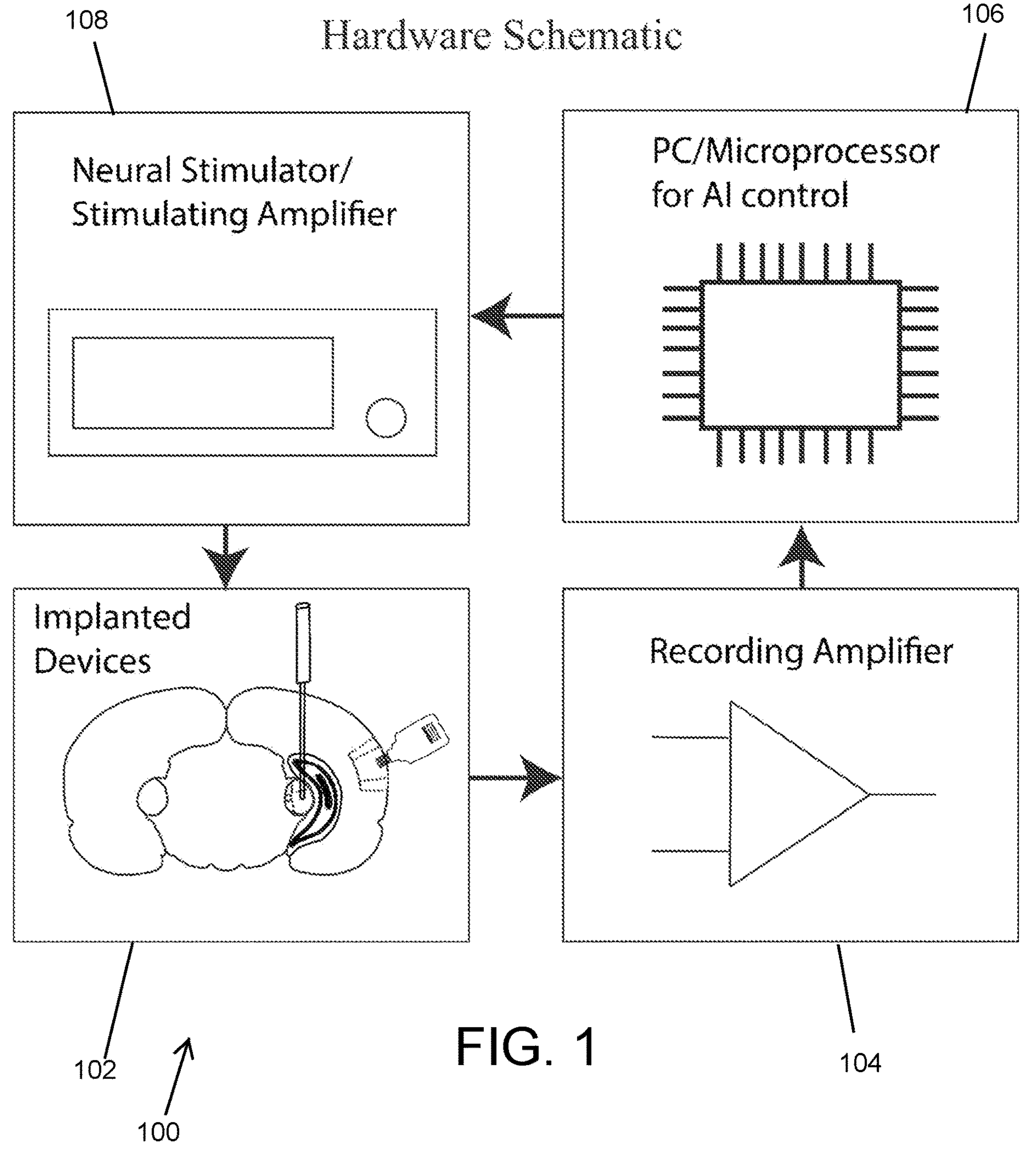
FIG. 1 is a schematic view of a neuromodulation system, according to one embodiment of the present disclosure.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. “A” and “an” as used herein indicate “at least one” of the item is present; a plurality of such items may be present, when possible. Except where otherwise expressly indicated, all numerical quantities in this description are to be understood as modified by the word “about” and all geometric and spatial descriptors are to be understood as modified by the word “substantially” in describing the broadest scope of the technology. “About” when applied to numerical values indicates that the calculation or the measurement allows some slight imprecision in the value (with some approach to exactness in the value; approximately or reasonably close to the value; nearly). If, for some reason, the imprecision provided by “about” and/or “substantially” is not otherwise understood in the art with this ordinary meaning, then “about” and/or “substantially” as used herein indicates at least variations that may arise from ordinary methods of measuring or using such parameters.

Although the open-ended term “comprising,” as a synonym of non-restrictive terms such as including, containing, or having, is used herein to describe and claim embodiments of the present technology, embodiments may alternatively be described using more limiting terms such as “consisting of” or “consisting essentially of.” Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of “from A to B” or “from about A to about B” is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3,1-2, 2-10, 2-8, 2-3, 3-10, 3-9, and so on.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As shown in FIG. 1, the system 100 includes a sensor 102, a recording amplifier 104, a processor 106, and a stimulator 108. The neuromodulation system 100 may be configured to provide stimulation and control of an intended neural target. The recording amplifier 104 may be electrically coupled to the sensor 102. The recording amplifier 104 may be configured to read and process stimuli, such as neural actively, detected by the sensor 102. The recording amplifier 104 may be further configured to output a signal based on the processed stimuli. The processor 106 may be communicatively coupled to the recording amplifier 104. The processor 106 may execute steps to monitor the signal provided by the recording amplifier 104 and output an instruction based on the signal. The stimulator 108 may be communicatively coupled to the processor 106. The stimulator 108 may be configured to provide a non-binary stimuli to the intended target based on the instruction from the processor 106. As a non-limiting example, the neuromodulation system 100 may be configured to provide stimulation and control of a nervous system of a human or animal subject for the purpose of clinical restoration of neural function or basic science studies in neural dynamics. In certain circumstances, the sensor 102 may be provided as a non-invasive device such as an optical sensor, an epicutaneous sensor, or a similar sensor. Alternatively, the sensor 102 may be provided as an implantable device that is configured to be inserted subcutaneously into a patient. It should be appreciated that the sensor 102 may include any number of sensors and any combination of different sensors, within the scope of the present disclosure.

The non-binary stimuli includes variable stimulation parameters which may have three or more states. For instance, unlike binary stimuli which is limited to only an on state and an off state, the non-binary stimuli may provide variable stimulation parameters such as stimulation amplitude, a number of pulse stimuli, and/or a duration of stimuli. More specifically, the stimulation amplitude may include a zero-amplitude state, a low amplitude state, and a high amplitude state. The number of pulse stimuli may be varied to provide no stimuli, a single pulse stimuli, and a plurality of pulse stimuli. The duration of stimuli may include no stimuli, a brief period of stimuli (such as one second), and an extended period of stimuli (such as five seconds). One skilled in the art may select other suitable variable stimulation parameters and/or the number of non-binary stimuli states, within the scope of the present disclosure.

In certain circumstances, the neuromodulation system 100 may be provided as a single device containing each of the sensor 102, the recording amplifier 104, the processor 106, and the stimulator 108. In a specific example, the neuromodulation system 100 provided as the single device may be configured to be at least partially or completely implantable subcutaneously into a patient. Alternatively, the neuromodulation system 100 may be provided as separate components where the sensor 102, the recording amplifier 104, the processor 106, and the stimulator 108 may be individual structures that are electrically coupled to one another.

With reference to FIGS. 1-7, the processor 106 may have certain functionalities that may be performed by various components. For example, the processor 106 may include certain artificial intelligence features, such as a reinforcement learning module having reinforcement learning capabilities. As used herein, reinforcement learning should be understood as a set of statistical machine learning algorithms in which computational agents learn to take actions in environments through repeated iterations in the environment. In other words, the processor 106 may determine a statistical model based on the signal from the recording amplifier 104, and the processor 106 may apply the non-binary stimulation based on the statistical model. The processor 106 may then quantify an environmental response based on the non-binary stimulation and determine if another and/or a different non-binary stimulation is necessary. More specifically, the computational agent actions may include evoked neural activity in response to a stimulus to maximize a set reward, known in this disclosure as a metric mathematically modeling desired neural dynamics, as a non-limiting example. Reinforcement learning also can refer to that of classical or deep reinforcement learning where deep neural networks are used as a central aspect of the predetermined sets of instructions. Also as used herein, the predetermined sets of instructions may refer to the implementation of a set of processes implemented as a processor program (also known as program, script, code, or software application) implemented on a personal processor (also known as PC or processor) or real time embedded processor (also known as microprocessor or embedded system) or across many processors. The term processor refers to general purpose processors, graphics processing units (also known as GPUs), digital signal processors (also known as DSPs), and micro-processing units. In a specific example, the processor 106 may include a higher load processor, such as the INTEL CORE® i7 processor or the XEON® processor which are both commercially available from Intel Corporation. Where the neuromodulation system 100 is configured to be embedded into a patient, the processor 106 may require more specialized hardware that is minimally sized and capable of running efficiently. As non-limiting examples, the embedded processor 106 may include the AM57x™ microprocessor and/or the C66™ series digital signal processors commercially available from Texas Instruments Incorporated, the SHARC® series commercially available from Analog Devices, Inc., and/or the use of lower power ARM processors in conjunction with the MAX78000™ Artificial Intelligence microcontroller, which is commercially available from Maxim Integrated Products, Inc.

In certain circumstances, the processor 106 may include certain specialized functions. For instance, the processor 106 may classify data to enhance the efficiency of the neuromodulation system 100. The data may include quantified metrics of the environmental response after a corrective stimulation has been applied. As a non-limiting example, the quantified metrics of the environmental response may include if the corrective stimulation to the neural state was adequate to cause the environmental response to achieve a desired state. It should be understood that the neural state may include the firing patterns from one or more neurons as measured by action potential events, a pattern of oscillatory activity from a plurality of neurons as measured as an emergent continuous electrical signal, or that of neural patterns which give rise to an outward behavioral action. The desired state may be understood to include firing patterns that may result in an advantageous patient response. The quantified metrics may also include statistics of overstimulation or aberrant stimulation, which may cause an unintended response in an adjacent neural environment. The data may also include a record of the parameters measured by the sensor 102 and/or the recording amplifier 104. The data may be collected to learn from and optimize the actions taken by the neuromodulation system 100. In a specific, non-limiting example, the processor 106 may record the actions and/or paths taken by the neuromodulation system 100 and the effect those actions had on the neural environment in response, creating an action/response relationship of data. The processor 106 may learn from itself by optimizing any future actions from the neuromodulation system 100 by analyzing this action/response relationship of data, thereby enhancing the effectiveness and efficiency of the neuromodulation system 100.

Further specialized functions of the processor 106 may include certain autonomous features. For instance, the processor 106 may have system driven capabilities which permit the neuromodulation system 100 to autonomously select which parameters to measure, the timing of the corrective stimulation, the strength of the corrective stimulation, and/or the desired target of the corrective stimulation. However, in a specific example, a user of the neuromodulation system 100 may manually input certain threshold limits intended to militate against undesired effects such as overstimulation of the nervous system. Advantageously, where the neuromodulation system 100 includes system driven capabilities, the neuromodulation system 100 may more efficiently and effectively deliver corrective stimulations by analyzing the most statistically significant parameters, whereas known user-driven systems may have an increased risk of error where the user is selecting which parameters the neuromodulation system 100 should analyze. In other words, the system driven capabilities of the neuromodulation system 100 may militate against information bias which may be more prevalent in known user-driven systems. Desirably, the system driven capabilities of the neuromodulation device may also militate against generalizing the treatments or the parameters monitored between patients. Known user-driven systems do not account for interpatient variability. It is a concern in known user-driven systems that a user would likely monitor the parameters that were previously acceptable based on a history of different patients. Conversely, the system driven capabilities of the present disclosure may monitor the unique neural environment of each patient and may autonomously select which parameters and actions the neuromodulation system 100 should use according to the individual needs of each patient, thereby enhancing the effectiveness of the treatment.

In certain circumstances, the neuromodulation system 100 may include ways to reduce the need of routine maintenance and calibration. For instance, the processor 106 of the neuromodulation system 100 may be configured to continuously monitor the neural environment of the patient and autonomously determine which parameters to analyze and optimize. Known methods of neural stimulation may require routine recalibrations which may undesirably require the patient to regularly commute to a clinic or facility. Advantageously, the neuromodulation system 100 of the present disclosure may effectively recalibrate substantially continuously and autonomously without requiring the patient to visit a clinic or facility.

Known methods of neural stimulation operate in an open loop fashion, whereby stimulation is applied independent of resulting neural activity which increases the likelihood of undesirable off-target affects and neural adaptation to the stimulation. In certain circumstances, the processor 106 may be configured as a closed loop system that includes a feedback feature that may monitor signals and deliver a response based on those signals. For instance, the closed loop system may include the process of sensing the current neural dynamics produced by the brain and using that information to actuate via stimulation directed changes in brain state. In a specific example, the neuromodulation system 100 of the present disclosure may utilize a stimulation system that operates in a closed loop system that is continuously measuring and searching for both desired and abhorrent neural activity and applying corrective stimulation when an abnormal activity, such as highly correlated activity found in epilepsy or Parkinson's disease, is detected. It should be appreciated that the present disclosure may be utilized to detect many diseases that have purported biomarkers. For instance, beta oscillations may be detectable biomarkers in Epilepsy and Parkinson's Disease that the present technology may be configured to identify. In a specific example, the continuous measuring and application of corrective stimulations may desirably be applied in real time allowing the corrective stimulations to be provided more quickly. Desirably, the response stimulations may also be more effectively applied since the real time data would reflect more accurate information regarding the current environmental conditions, such as the current neural dynamics produced by the brain.

In certain circumstances, as shown in FIG. 1, neural activity may be read and processed by the recording amplifier 104. In a specific example, the recording amplifier 104 may include a neural recording amplifier 104 resulting from stimulation via a stimulation amplifier or similar devices. Online analysis of neural signals may be performed on the processor 106 which may also be used for implementation of reinforcement learning algorithms. Learning representations from the learning algorithm may then be used to apply new stimulation towards a desired firing pattern or brain state. In other words, the present technology may build at least one statistical model and utilize a reinforcement learning methodology to apply a unique corrective action to the neural state based on the needs detected by the at least one statistical model. In certain circumstances, the implementation of discrete amplifiers and processors linked via a wireless communication protocol may enable the neuromodulation system 100 to be provided as separate components. In a specific example, the sensor 102, the recording amplifier 104, and/or the stimulator 108 may wirelessly communicate with the processor 106. In a more specific example, the wireless communication protocol may include the use of Wi-Fi, Bluetooth connectivity, and/or other similar wireless communication systems. In certain circumstances, the neuromodulation system 100 may be implemented with each of the sensor 102, the recording amplifier 104, the processor 106, and the stimulator 108 may be contained within a single device, such as a fully implantable microprocessor. Advantageously, where the neuromodulation system 100 is contained within a single device, the neuromodulation system 100 may be more portable and easier to provide the neuromodulation system 100 to more remote locations. Desirably, a patient may not be constrained to staying in a single location, such as a hospital, as the neuromodulation system 100 is monitoring and providing stimulations. In a specific example, the present disclosure may provide an implementation of reinforcement learning which creates real-time statistical models of current and recent past neural states which actively and automatically learns stimulation paradigms which create paths from pathological to nominal brain states.

Evoked neural signals may be obtained in a multiplicity of ways. In certain circumstances, neural recording electrode(s) may be fully implanted into the body, such as penetrating depth arrays which may be used to record individual or network neuron activity as well as local field potentials as a marker of network activity. Other implanted devices consist of electrocorticography (ECoG) or micro electrocorticography (μECoG) arrays for measuring bulk field responses on the surface of the brain. Alternatively, the neuromodulation system 100 may utilize non-invasive neural recording methods, such as electroencephalography (EEG) and magnoencephalography (MEG) involving bulk recording of neural field activity from the surface of the skin. One skilled in the art may select other suitable devices for sensing and/or measuring neural field activity, within the scope of the present disclosure.

Similar to the recording arrays, there are a multiplicity of stimulation designs which may be used. For instance, stimulation may be provided through artificial stimulation via the application of electric fields, currents, or optical stimulation. Alternatively, the neuromodulation system 100 may include the utilization of naturalistic stimulation, such as auditory, motor, visual, etc. stimuli. In other words, the neuromodulation system 100 of the present disclosure may use a sensory input, such as evoked neural activity resulting from auditory, motor, visual, or similar stimuli in place of an artificial stimulator for use in optimizing sensory inputs for desired brain activity. A skilled artisan may select other suitable stimulation designs, within the scope of the present disclosure.

Figure 2:
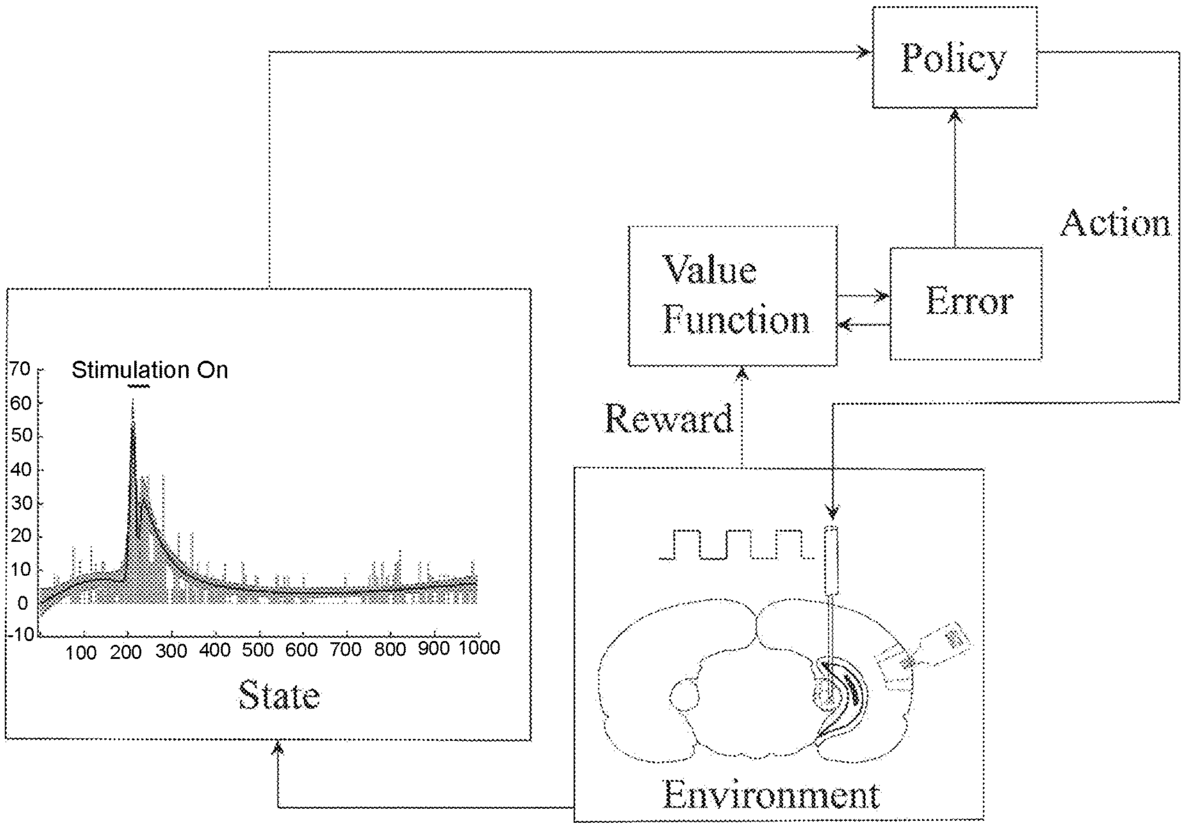
FIG. 2 is a schematic view of the neuromodulation system implementing a reinforcement learning system, further depicting where neural firing patterns are recorded and analyzed and passed to a processor to learn stimulation policies, to change stimulation parameters, and to drive firing activity towards desired patterns, according to one embodiment of the present disclosure.

Known methods of neuromodulation utilize simple threshold detectors which lack the ability to quantify dynamics of neural activity which may be important for disease treatment. Conversely, the stimulation provided by the neuromodulation system 100 in the present disclosure may be advantageously controlled using reinforcement learning to build up statistical models of the relationship between neural firing patterns and apply stimuli to drive neural firing patterns and brain state towards a desired target. As shown in FIG. 2, reinforcement learning may be implemented between recording and stimulating electrodes. In the reinforcement learning paradigm, a state (S) may be defined as the current position or situation an agent is in while in a given environment (E). For instance, the environment may be the brain and associated physiological firing properties with a given state being the current firing pattern observed. This firing pattern can be quantified in a variety of ways, such as neuron action potential firing rate, amplitude of local field potentials, correlation of firing between two neurons, etc. The state may be defined in an application specific manner. An action may be defined as the process taken in response to the current state in the environment. In a specific example, the action may include variable stimulation parameters, such as stimulation amplitude, number of pulse stimuli, and duration of stimuli but can consist in any number or combination of parameters. The processor 106 may then quantify the value of neural activity deficiency remaining in the current state versus transitioning to a new state which is dependent on measured error between current state and the desired state and current and past rewards for transitioning between states.

Figure 3:
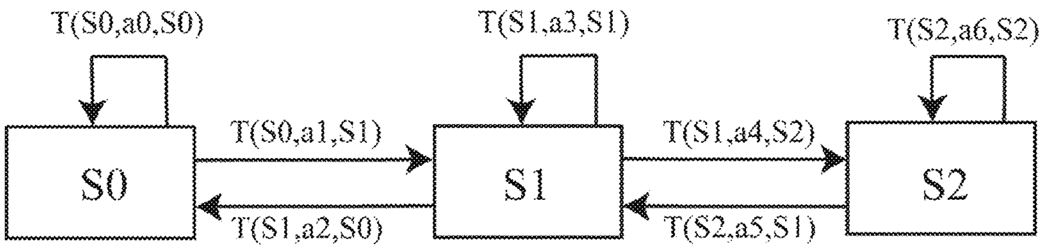
FIG. 3 depicts the Markov decision process underpinning statistical models of neural state transitions utilized by the neuromodulation system, according to one embodiment of the present disclosure.

As shown in FIG. 3, the states may be modeled as a Markov decision process in which transitions between states are stochastic, marked by transition probabilities $T(S_i, a_j, S_k)$ which is the probability of moving from state $S_i$ to state $S_k$ by taking action $a_j$. State transitions are independent of past states, but state-reward relationships are used to build up a policy function, as shown in FIG. 2, which is used to model mappings between current neural firing patterns and applied stimuli and series of stimulation actions to take to move to desired states.

Figure 4:
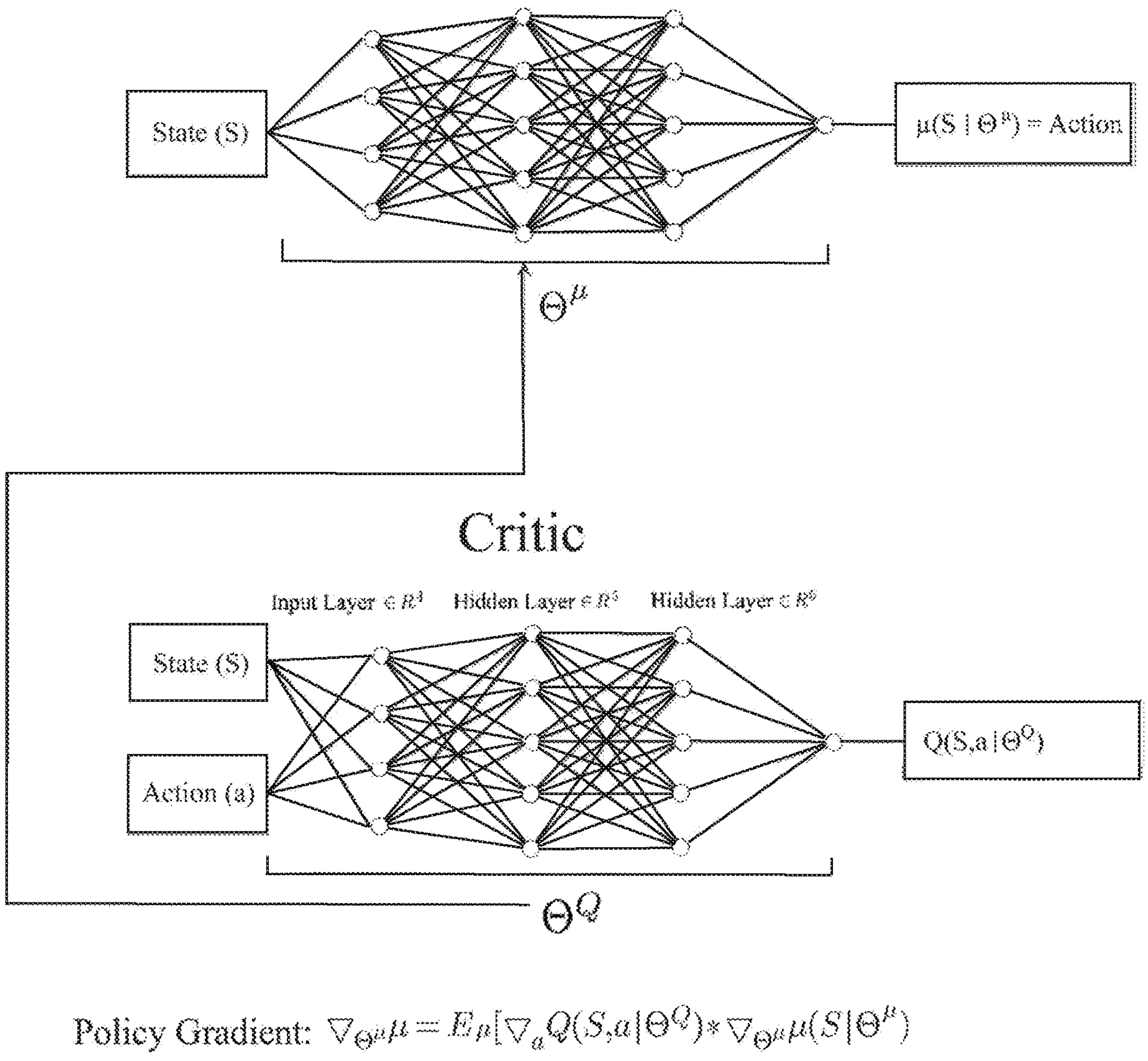
FIG. 4 is a schematic view of a deep neural network used by the neuromodulation system to derive (actor) and refine (critic) statistical models of the brain state environment, further depicting a non-limiting example of the algorithm finding a target neural firing pattern, according to one embodiment of the present disclosure.

There may be many different implementations of the policy function. In certain embodiments, a set of deep neural networks may be used to build and refine the policy gradient, as shown in FIG. 4. In this "actor-critic" model, in which the actor encodes the policy function mapping state to action spaces and chooses the actions, such as the stimulus, which is further refined by a secondary network (the critic) which refines the function by evaluating how successful a given action taken by the actor was and how it should adjust to minimize current and future errors. One skilled in the art may select other suitable reinforcement learning algorithms, within the scope of the present disclosure.

Of upmost importance to the performance of a reinforcement learning algorithm is the choice of reward function which fundamentally dictates and quantifies stimulation goals. For controlling the dynamics of single neurons, the present disclosure utilizes a mean-square error loss function, quantified in the following formula:

$$R_{MSE} = \frac{1}{n}\sum_{i}^{n}(x_{target} - x_{observed})^2$$

Where n is the number of stimulation trials, $x_{target}$ is the desired neural state and $x_{observed}$ is the recorded neural state. This reward function is asymptotically the maximum likelihood estimator for the process, making it a suitable choice for inference and for use in the present disclosure. However, certain embodiments of the neuromodulation system 100 may have tailored reward functions suited to the number of recording and stimulating electrodes or to specific goals for treatment. The present disclosure may also include software and hardware stimulus limits to militate against any stimulus choice rising to ablative thresholds.

In certain circumstances, the present disclosure may include the ability for the processor 106 to train responses across multiple electrodes and/or stimulators to a single reward function or to unique reward functions across spatially disparate stimulation and recording electrodes. In a specific example, neural populations may be heterogeneous, with different regions potentially controlling or perceiving different motor actions or senses, respectively. Advantageously, in regions within this heterogeneity, the ability for the processor 106 to train responses across multiple electrodes and/or stimulators to a single reward function or to unique reward functions across spatially disparate stimulation and recording electrodes may allow for more robust control.

In certain circumstances, the neuromodulation system 100 may include a kit. As shown in FIG. 1, the kit may include a sensor 102, a recording amplifier 104, a processor 106, and a stimulator 108. In a specific example, the sensor 102 may include a plurality of sensors. In a more specific example, one or more of the sensors, the recording amplifier 104, the processor 106, and the stimulator 108 may be configured to be electrically coupled to another of the sensor 102, the recording amplifier 104, the processor 106, and/or the stimulator 108. In another specific example, one or more of the sensors, the recording amplifier 104, the processor 106, and the stimulator 108 may be configured to wirelessly communicate to another of the sensor 102, the recording amplifier 104, the processor 106, and/or the stimulator 108.

Figure 8:
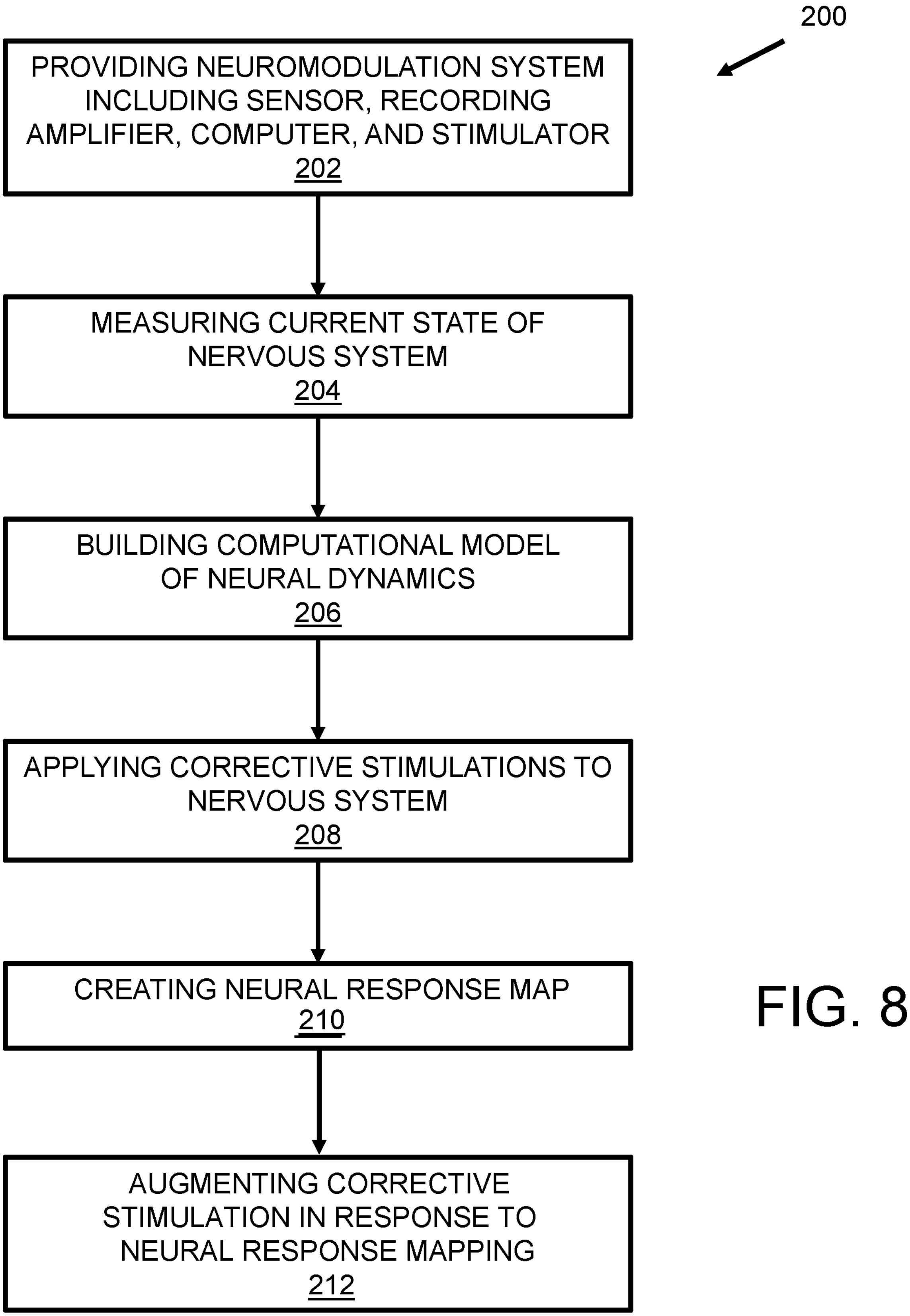
FIG. 8 is a first method for using the neuromodulation system, according to one embodiment of the present disclosure.

Various ways of using the neuromodulation system 100 are provided. As shown in FIG. 8, a method 200 may include a step 202 of providing the neuromodulation system 100 having a sensor 102, a recording amplifier 104, a processor 106, and a stimulator 108. The method 200 may include a step 204 of observing and/or measuring the current state of the nervous system by utilizing the sensor 102. The sensor 102 may be one of an implanted epicutaneous, optical, or similar sensor. Next, the processor 106 may build and refine computational models of neural dynamics using a method of reinforcement learning. Then, corrective stimulations may be applied to the nervous system to steer activity towards a desired state. This may include calculating an error between current and desired states. The corrective stimulations may include targeted electrical, optical, or similar stimulations. It should be appreciated that the system may reach a steady state after one or more iterations of corrective stimulations. Afterwards, the environment may be monitored to feed back a current state and a reward or error associated with the movement between states. A neural response map may be created by the processor 106 of stimulation to response relationships to maintain desired neural dynamics. In certain circumstances, the neuromodulation system 100 may continue to augment and improve stimulation to neural response mappings.

Figure 9:
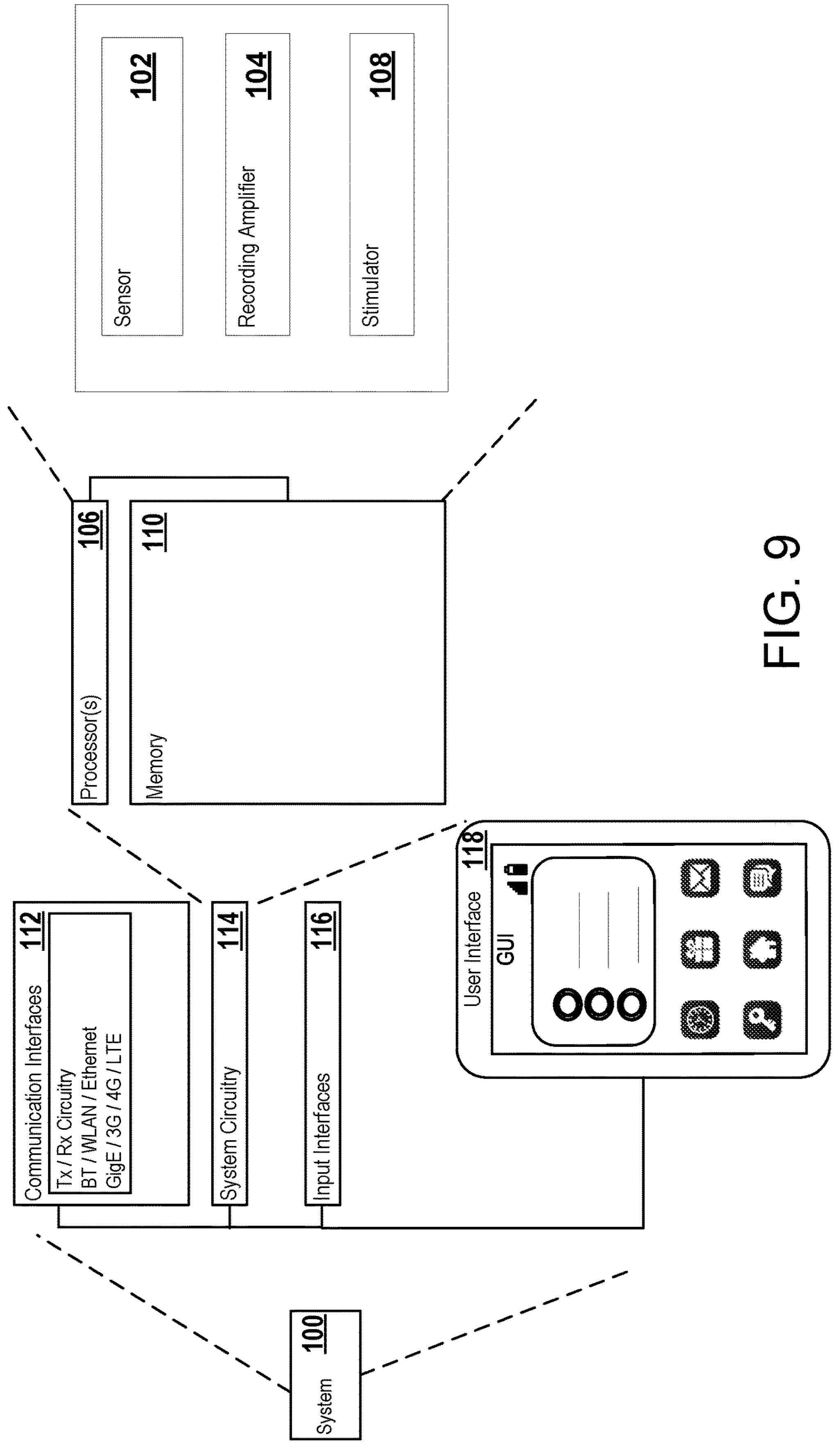
FIG. 9 is a schematic diagram illustrating another example of the neuromodulation system, according to one embodiment of the present disclosure.

FIG. 9 illustrates a second example of the system 100. The system 100 may include communication interfaces 112, input interfaces 116 and/or system circuitry 114. The system circuitry 114 may include a processor 106 or multiple processors. The processor 106 or multiple processors execute the steps to monitor a first signal of neural activity, determine a statistical model based on the first signal, apply a non-binary stimulation based on the statistical model, monitor a second signal of neural activity, and output a quantified metric of an environmental response from the second signal. Alternatively, or in addition, the system circuitry 114 may include memory 110.

The processor 106 may be in communication with the memory 110. In some examples, the processor 106 may also be in communication with additional elements, such as the communication interfaces 112, the input interfaces 116, and/or the user interface 118. Examples of the processor 106 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor 106 may be one or more devices operable to execute logic. The logic may include computer executable instructions or computer code stored in the memory 110 or in other memory that when executed by the processor 106, cause the processor 106 to perform the operations the adaptive object detection framework 101, the multi-branch object detector 102, scheduler 104, and/or the system 100. The computer code may include instructions executable with the processor 106.

The memory 110 may be any device for storing and retrieving data or any combination thereof. The memory 110 may include non-volatile and/or volatile memory, such as a random access memory (RAM), a read-only memory (ROM), an erasable programmable read-only memory (EPROM), or flash memory. Alternatively or in addition, the memory 110 may include an optical, magnetic (hard-drive), solid-state drive or any other form of data storage device. The memory 110 may include at least one of the sensor 102, the recording amplifier 104, the stimulator 108. Alternatively or in addition, the memory 110 may include any other component or sub-component of the system 100 described herein.

The user interface 118 may include any interface for displaying graphical information. The system circuitry 114 and/or the communications interface(s) 112 may communicate signals or commands to the user interface 118 that cause the user interface to display graphical information. Alternatively or in addition, the user interface 118 may be remote to the system 100 and the system circuitry 114 and/or communication interface(s) may communicate instructions, such as HTML, to the user interface to cause the user interface to display, compile, and/or render information content. In some examples, the content displayed by the user interface 118 may be interactive or responsive to user input. For example, the user interface 118 may communicate signals, messages, and/or information back to the communications interface 112 or system circuitry 114.

The system 100 may be implemented in many different ways. In some examples, the system 100 may be implemented with one or more logical components. For example, the logical components of the system 100 may be hardware or a combination of hardware and software. In some examples, each logic component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each component may include memory hardware, such as a portion of the memory 110, for example, that comprises instructions executable with the processor 106 or other processor to implement one or more of the features of the logical components. When any one of the logical components includes the portion of the memory that comprises instructions executable with the processor 106, the component may or may not include the processor 106. In some examples, each logical component may just be the portion of the memory 110 or other physical memory that comprises instructions executable with the processor 106, or other processor(s), to implement the features of the corresponding component without the component including any other hardware. Because each component includes at least some hardware even when the included hardware comprises software, each component may be interchangeably referred to as a hardware component.

Some features are shown stored in a computer readable storage medium (for example, as logic implemented as computer executable instructions or as data structures in memory). All or part of the system 100 and its logic and data structures may be stored on, distributed across, or read from one or more types of computer readable storage media. Examples of the computer readable storage medium may include a hard disk, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system 100 may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL).

All of the discussion, regardless of the particular implementation described, is illustrative in nature, rather than limiting. For example, although selected aspects, features, or components of the implementations are depicted as being stored in memory(s), all or part of the system or systems may be stored on, distributed across, or read from other computer readable storage media, for example, secondary storage devices such as hard disks and flash memory drives. Moreover, the various logical units, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

EXAMPLE

Rats were implanted in the auditory thalamocortical pathway with a stimulating infrared neural stimulation optrode into the medial geniculate body and a multichannel recording array into primary auditory cortex. The goal of these sessions where to drive neuron action potential firing rates to a desired target. As such, a real time action potential detection algorithm was implemented. Voltage waveforms recorded from auditory cortex were bandpass filtered between 300 and 5000 Hz. To detect action potentials within electrode voltage waveforms, a standard threshold detection method, as shown below, was used.

$$T_{Thresh} \rightarrow \frac{dv_i}{dt} > stdmin * MAD_{est}$$

Where stdmin is set apriori to 3.8-4 contingent on implicit electrode noise, $MAD_{est}$ is the median amplitude deviation, as shown below.

$$MAD_{est} = \text{median}\left(\frac{v}{0.6745}\right)$$

The $MAD_{est}$ may constitute an estimator which asymptotically approaches the $75^{th}$ percentile of the unit normal distribution. Voltage deflections were counted as spikes if the instantaneous time derivative of the voltage was greater than $T_{thresh}$ and does not fall in a dead time refractory window from a previous threshold crossing.

Each stimuli was presented ten times with spikes counted in every trial. After the tenth trial, peristimulus time histograms (PSTH) were generated by dividing each trial into bins of 5 ms, counting all spikes that fall into a given bin across all trials and normalized by the number of trials multiplied by bin size. A continuous rate firing function was then estimated using Bayesian adaptive regression splines. It should be appreciated that while this example shows the control of spike firing rate density functions, the present disclosure is not limited to this and can fit any type of evoked activity, within the scope of the present disclosure.

Figure 5:
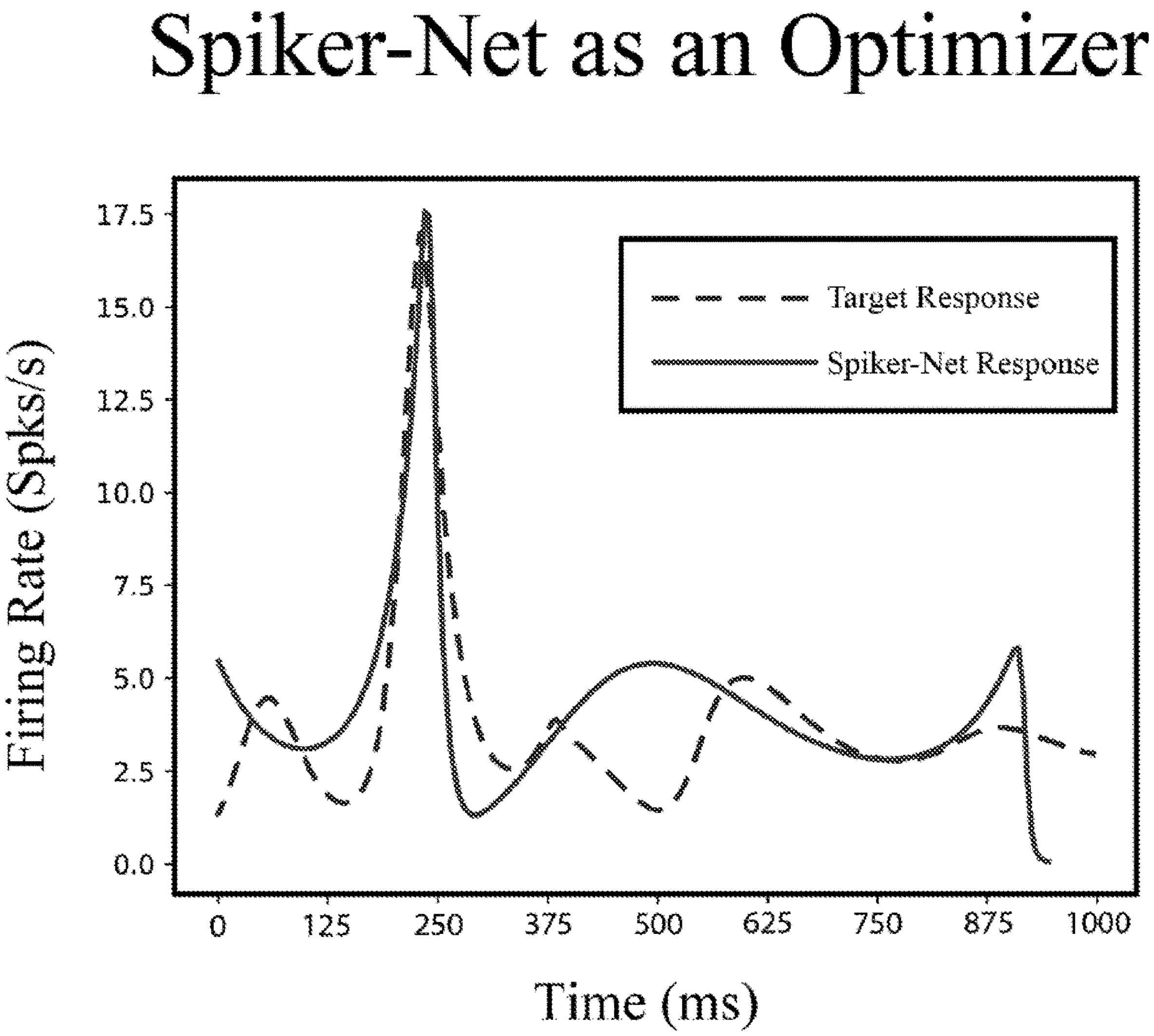
FIG. 5 is a line chart depicting an algorithm that may be utilized by the neuromodulation system to find a target neural firing pattern, according to one embodiment of the present disclosure.
Figure 6A:
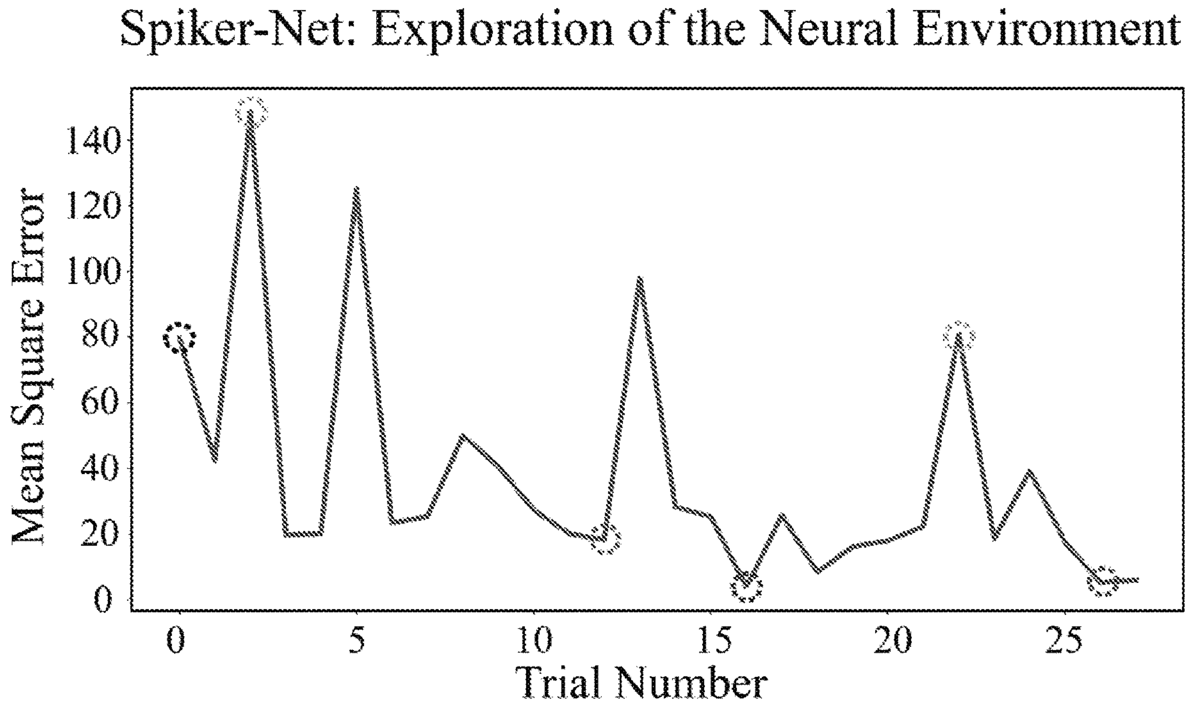
FIG. 6A is a line graph illustrating how the neuromodulation system builds statistical models of neural activity by searching stimulation parameters to find a series of stimulation patterns leading to desired neural firing states, according to one embodiment of the present disclosure.
Figure 6B:
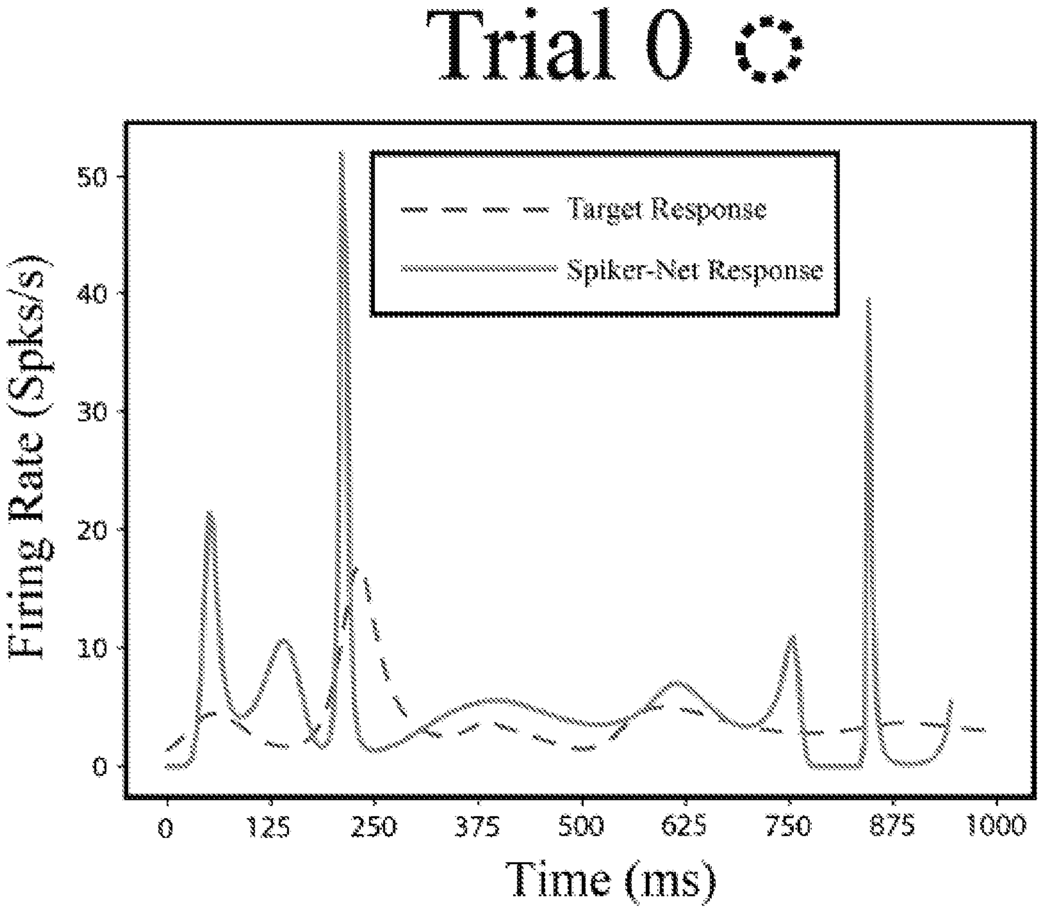
FIG. 6B is a line graph illustrating a starting point, at trial 0, of the neural activity for building the statistical model, as shown in FIG. 6A.
Figure 6C:
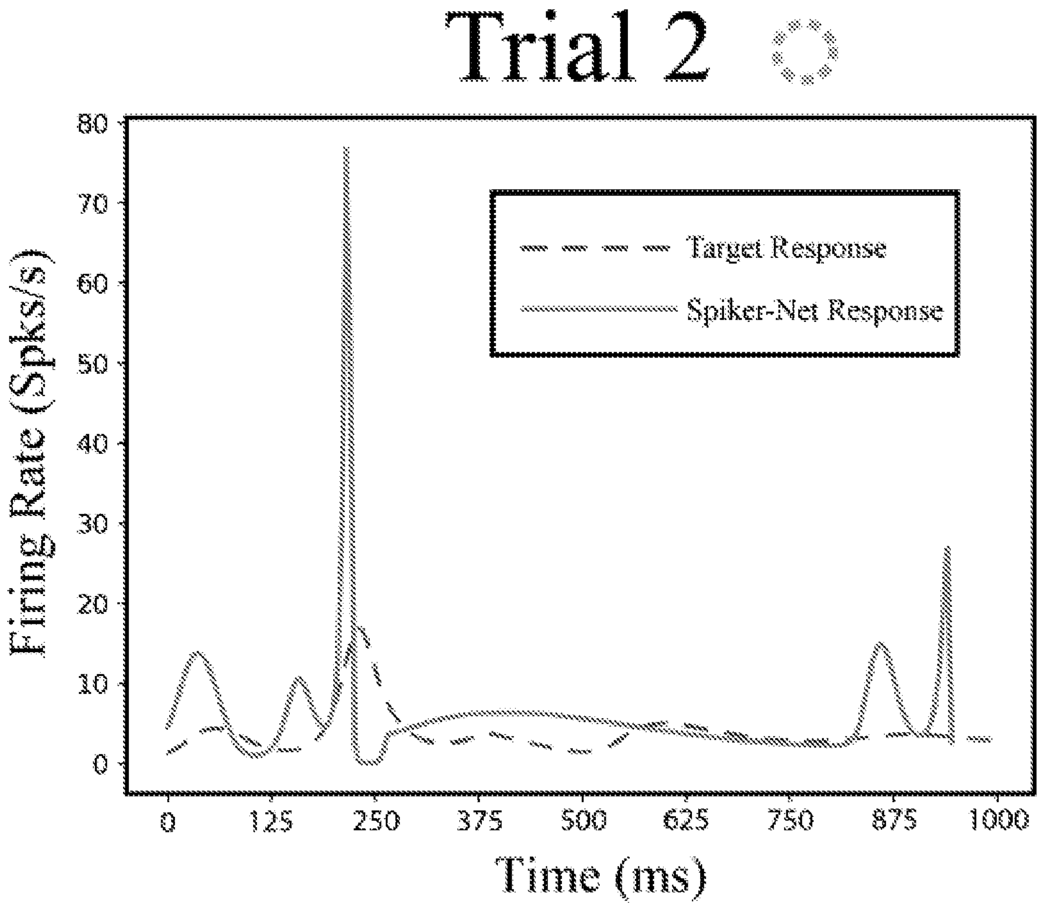
FIG. 6C is a line graph illustrating the neural activity for building the statistical model at trial 2, further depicting onset-inhibition, as shown in FIG. 6A.
Figure 6D:
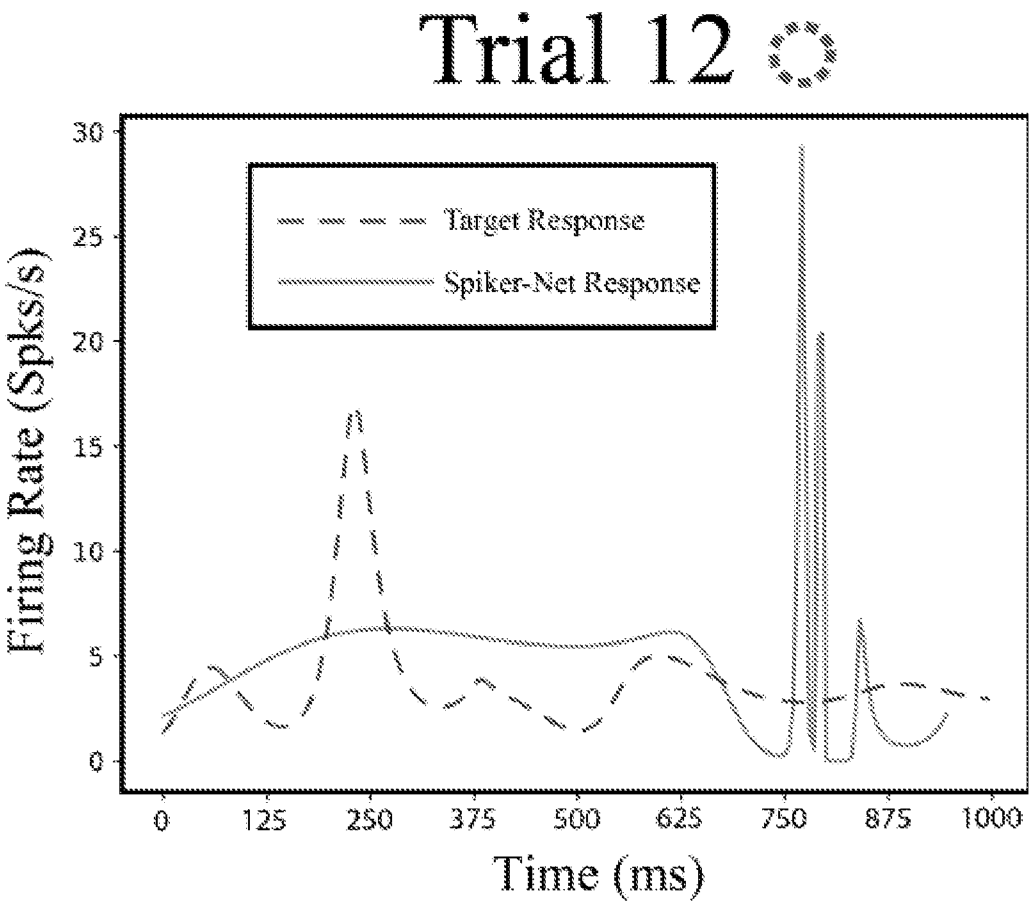
FIG. 6D is a line graph illustrating the neural activity for building the statistical model at trial 12, further depicting a rebound, as shown in FIG. 6A.
Figure 6E:
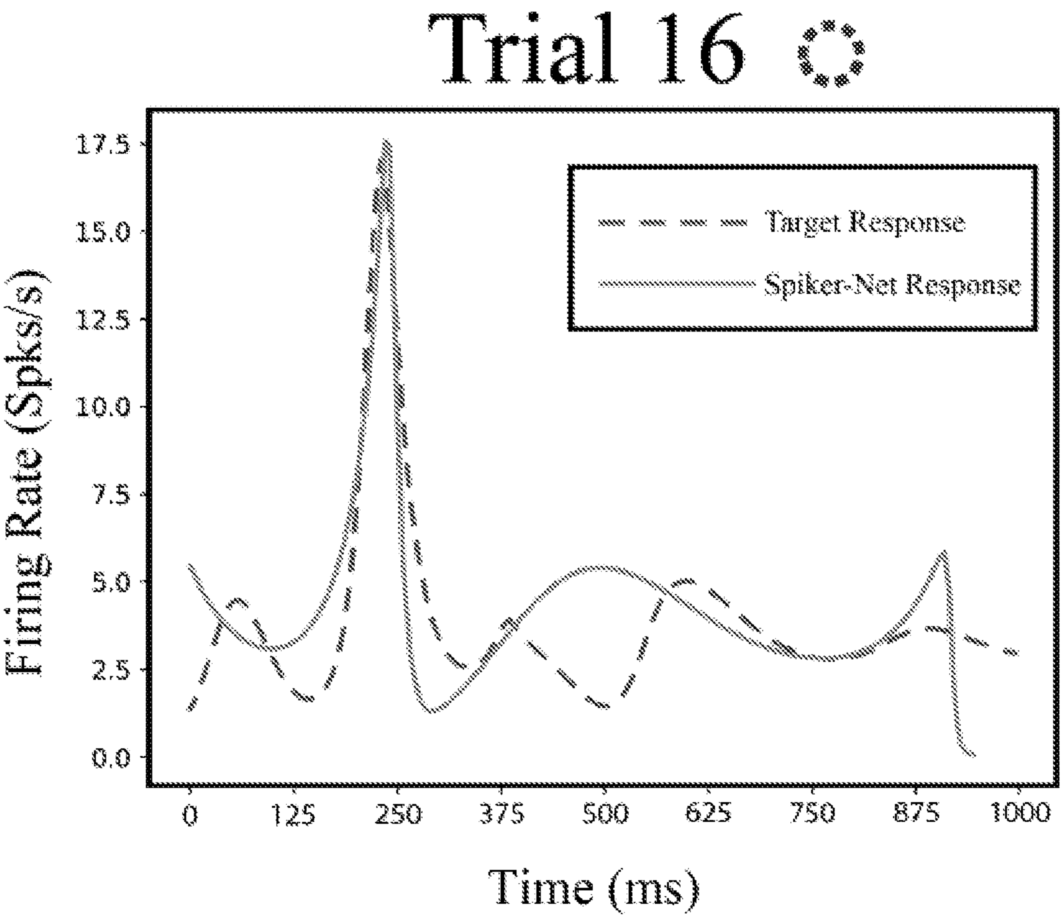
FIG. 6E is a line graph illustrating the neural activity for building the statistical model at trial 16, as shown in FIG. 6A.
Figure 6F:
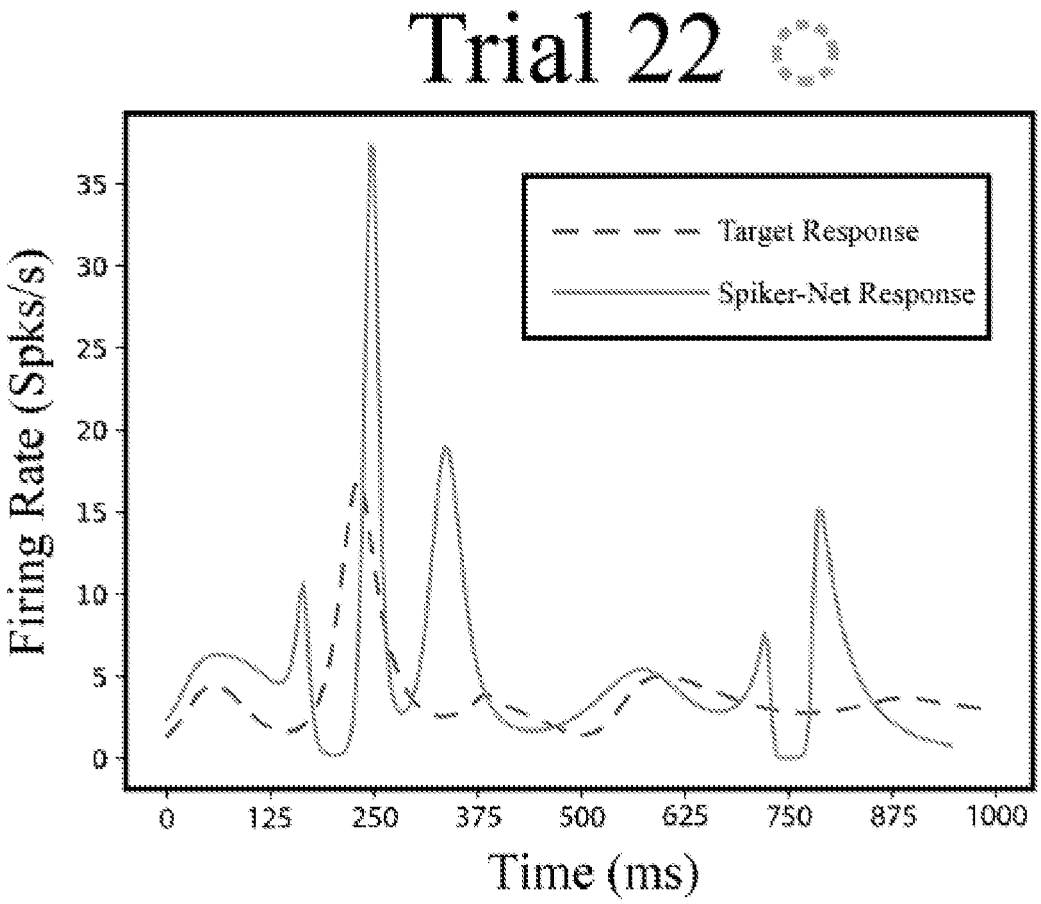
FIG. 6F is a line graph illustrating the neural activity for building the statistical model at trial 22, further depicting a multiphasic response, as shown in FIG. 6A.
Figure 6G:
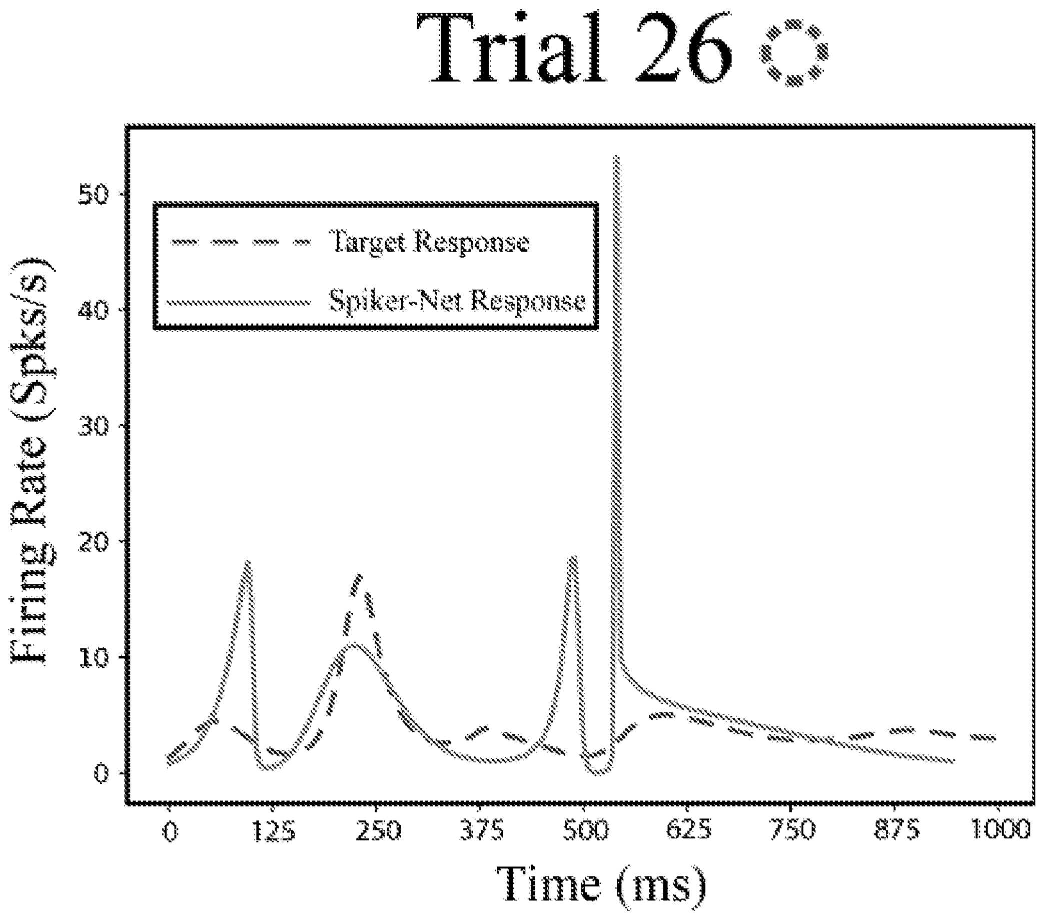
FIG. 6G is a line graph illustrating the neural activity for building the statistical model at trial 26, further depicting a multiphasic response, as shown in FIG. 6A.

Initial studies using the neuromodulation system 100 revolved around finding stimulation parameters which can drive current neural firing towards targeted brain-states. As shown in FIG. 5, a desired firing density curve was identified as an integral stimulus parameter. It should be appreciated that spontaneous firing activity (firing rates at times >275 ms) was not directly included in the reward function and not directly controllable. However, other embodiments of the present disclosure with larger stimulation channel densities could also fit spontaneous firing activity by modulating efferent projections or local interneurons.

A primary advantage in a reinforcement learning paradigm is the ability to quickly and effectively switch between exploration of an environment and objective tracking towards a target state. FIGS. 6A-6G demonstrate a sample learning trajectory and exploration of the neural space while showing tracking towards targeted brain states. A multiplicity of responses can be found even within a few numbers of trial, including onset-inhibition found in trial 2, rebound in trial 12, and multiphasic response found in trial 22 and 26. In this session, target solutions are also found relatively quick, after only 16 stimulus trials. Importantly, the searching space may be saved, and evoked responses learned to create a map of stimulus response relationships and how to move towards targeted responses given an observed brain state.

Figure 7A:
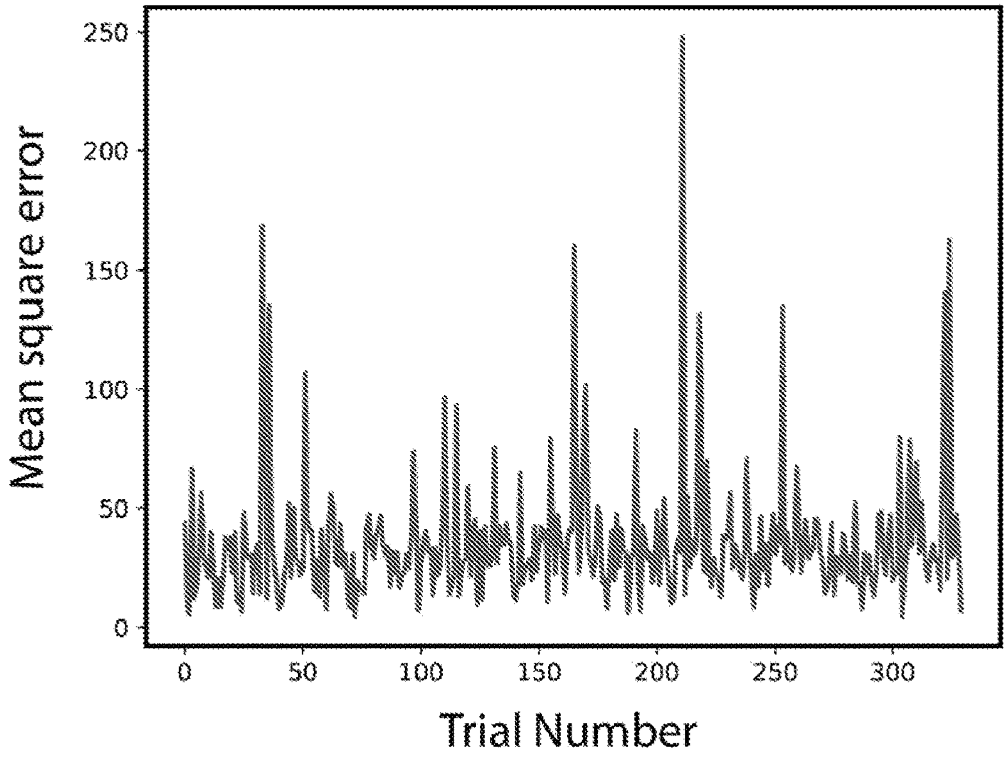
FIG. 7A is a line graph illustrating a search and return behavior of the neuromodulation system over long-term iterations, according to one embodiment of the present disclosure.
Figure 7B:
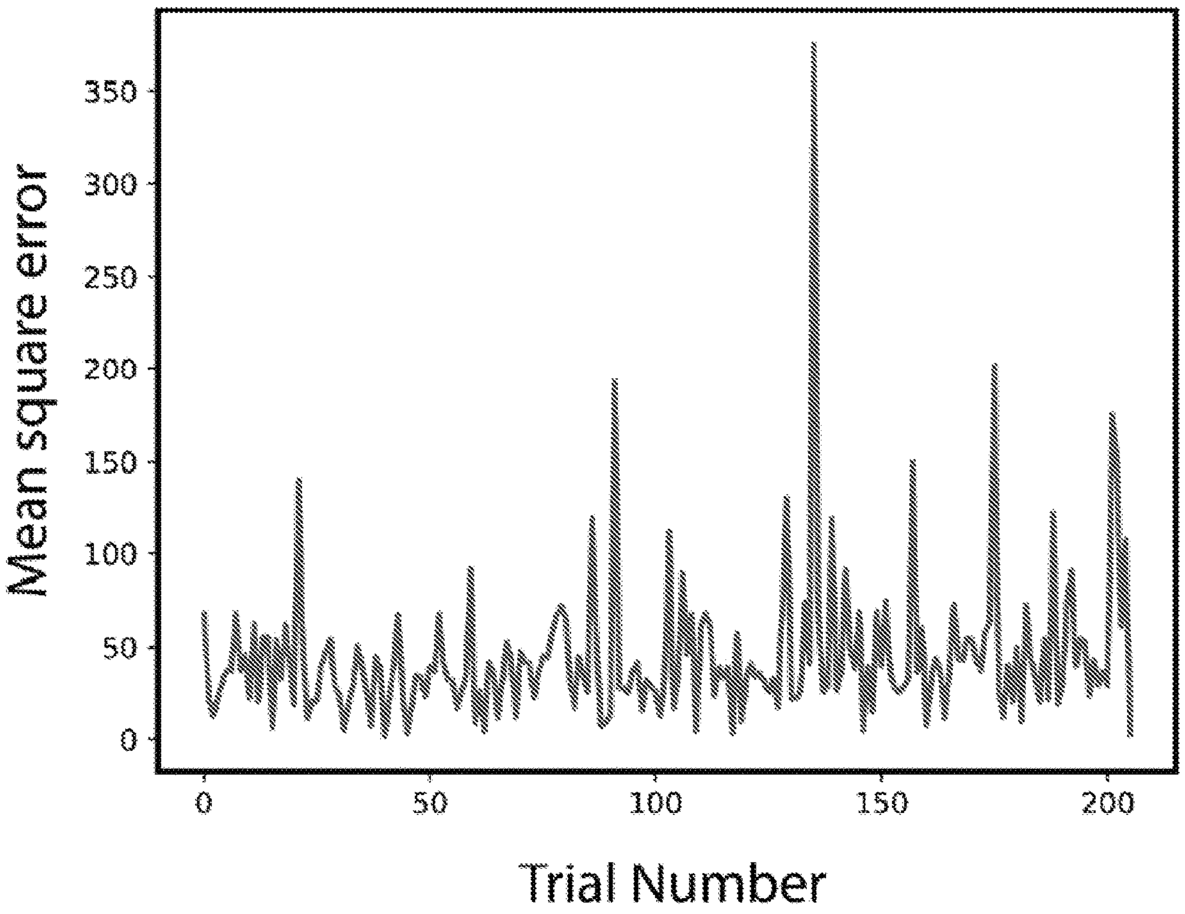
FIG. 7B is a line graph illustrating another search and return behavior of the neuromodulation system over long-term iterations, according to one embodiment of the present disclosure.

Another key advantage in reinforcement learning is the ability to continuously learn over time and update policies and actions based on time-series dynamics as opposed to learning through curated and biased training data sets. The present disclosure desirably builds a space environment representation of sequences of actions leading to a given neural firing pattern and how those patterns evolve through time. FIGS. 7A-7B demonstrate this learning through a paradigm in which target states are found, represented as low error with respect to the target brain state, and continued searching through searching of the environment. Training of this system 100 for clinical or scientific use may include various strategies. One such strategy may include training in discrete manner, where training and exploration create a singular model of the patients neural firing patterns in response to therapeutic stimuli and then a fixed stimulus to response map is implemented for the patient across many changing brain states. Another possible strategy is through continuous learning, in which the system constantly observes neural dynamics and reinitializes a stimulus to response map each time a brain state is found. An example of changing brain state may include transitions between sleep-wake states or across the continuum of arousal states.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A neuromodulation system configured to stimulate and control a nervous system, comprising:

a sensor that is configured to monitor the nervous system;

a recording amplifier that is electrically coupled to the sensor, the recording amplifier configured to read and process stimuli detected by the sensor, and output a signal;

a processor communicatively coupled to the recording amplifier, the processor executing steps to:

monitor the signal provided by the recording amplifier, implement a reinforcement learning algorithm to determine an optimal stimulation strategy based on a reward function, and output an instruction based on a policy derived from the reinforcement learning algorithm, wherein the reinforcement learning algorithm includes a critic module and an actor module, the critic module estimates a value function based on a neural state and an action and the actor module generates the instruction based on the value function, wherein the actor module and the critic module are trained using a neural dynamics model that adapts to patient-specific responses over time, the policy is refined based on reward signals derived from mean-square error between a target and an observed neural response, wherein the reward function is dynamically updated based on patient-specific neural biomarkers; and a stimulator communicatively coupled to the processor, the stimulator is configured to provide a non-binary stimulation based on the instruction provided by the processor;

wherein the processor is configured to implement a patient-specific stimulation policy using an actor-critic reinforcement learning architecture; and wherein the processor is a closed loop system, the processor continuously measures and searches for an aberrant neural activity corresponding to a deviation from a desired neural state, and autonomously delivers the instruction to the stimulator to apply the non-binary stimulation when an aberrant neural activity is detected.

2. The neuromodulation system of claim 1, wherein the non-binary stimulation includes variable stimulation parameters having three or more states.

3. The neuromodulation system of claim 2, wherein the variable stimulation parameters include at least one of a stimulation amplitude, a number of pulse stimuli, and a duration of stimuli.

4. The neuromodulation system of claim 1, wherein the sensor is a non-invasive device.

5. The neuromodulation system of claim 1, wherein the mean-square error loss is provided as a function of:

$$R_{MSE} = \frac{1}{n}\sum_{i}^{n}(x_{target} - x_{observed})^2.$$

6. The neuromodulation system of claim 1, wherein the neuromodulation system is provided as a single device that is configured to be one of partially and completely implantable subcutaneously.

7. The neuromodulation system of claim 1, wherein the processor outputs a quantified metric of an environmental response from the signal.

8. The neuromodulation system of claim 7, wherein the quantified metrics include statistics of at least one of over-stimulation and aberrant stimulation.

9. The neuromodulation system of claim 7, wherein the quantified metrics include a record of parameters measured by the sensor and/or the recording amplifier.

10. The neuromodulation system of claim 1, wherein the processor includes system driven capabilities to enable the neuromodulation system to autonomously select at least one of a parameter to measure, a timing of the non-binary stimulation, a strength of the non-binary stimulation, and a desired target of the non-binary stimulation.

11. The neuromodulation system of claim 1, wherein the processor autonomously recalibrates the neuromodulation system.

12. The neuromodulation system of claim 11, wherein the processor continuously recalibrates the neuromodulation system.

13. The neuromodulation system of claim 1, wherein the non-binary stimulation is applied in real time as the aberrant neural activity is detected.

14. The neuromodulation system of claim 1, wherein at least one of the sensor, the recording amplifier, and the stimulator wirelessly communicate with the processor.

15. The neuromodulation system of claim 1, wherein the stimulator includes a plurality of stimulators, and the processor is configured to train responses across the plurality of stimulators to one of a single reward function and a unique reward function across spatially disparate stimulators.

16. A processor configured to stimulate and control a nervous system, the processor executing steps to:

monitor a first signal of neural activity;

determine a statistical model based on the first signal;

apply a non-binary stimulation based on the statistical model;

monitor a second signal of neural activity;

implement an actor-critic reinforcement learning algorithm to derive a stimulation policy, wherein the actor generates stimulation instructions and the critic evaluates neural state transitions; and output an instruction based on the stimulation policy derived from the reinforcement learning algorithm, the stimulation policy is refined based on mean-square error between a target and observed neural response, updated continuously during operation.

17. A method of using a neuromodulation system configured to stimulate and control a nervous system, the method comprising the steps of:

providing the neuromodulation system having a sensor, a recording amplifier, a processor, and a stimulator, the sensor is configured to monitor the nervous system, the recording amplifier is electrically coupled to the sensor, the recording amplifier is configured to read and process stimuli detected by the sensor, and output a signal, the processor is communicatively coupled to the recording amplifier, the processor executing steps to monitor the signal provided by the recording amplifier, implement a reinforcement learning algorithm to determine an optimal stimulation strategy based on a reward function, and output an instruction based on a stimulation policy derived from the reinforcement learning algorithm that models neural dynamics and refines stimulation policies based on real-time reward signals, the stimulation policy is refined based on reward signals derived from mean-square error between a target and an observed neural response, wherein the reward function is dynamically updated based on patient-specific neural biomarkers, the stimulator is communicatively coupled to the processor, the stimulator is configured to provide a non-binary stimulation based on the instruction provided by the processor, and wherein the reinforcement learning algorithm includes an actor module and a critic module, the actor module generating stimulation instructions and the critic module evaluating neural state transitions, and wherein the actor module and the critic module are trained using a neural dynamics model that adapts to patient-specific responses over time;

monitoring neural stimuli of the nervous system using the sensor;

measuring the neural stimuli of the nervous system by using the recording amplifier;

quantifying, via the processor, a neural dynamics of the nervous system; and applying the non-binary stimulation to the nervous system.

18. The method of claim 17, further comprising a step of mapping the neural dynamics of the nervous system in response to the non-binary stimulation.

19. The method of claim 18, further comprising a step of augmenting the non-binary stimulation in response to mapping the neural dynamics of the nervous system.

* * * * *